United States Patent
Twersky

(10) Patent No.: US 12,178,263 B2
(45) Date of Patent: Dec. 31, 2024

(54) COOLING AND DRINKING VEST

(71) Applicant: Yitzchok Twersky, Brooklyn, NY (US)

(72) Inventor: Yitzchok Twersky, Brooklyn, NY (US)

( * ) Notice: Subject to any disclaimer, the term of this patent is extended or adjusted under 35 U.S.C. 154(b) by 210 days.

(21) Appl. No.: 17/948,864

(22) Filed: Sep. 20, 2022

(65) Prior Publication Data

US 2023/0301373 A1 Sep. 28, 2023

Related U.S. Application Data

(60) Provisional application No. 63/322,373, filed on Mar. 22, 2022.

(51) Int. Cl.
| | | |
|---|---|---|
| *A41D 13/005* | (2006.01) | |
| *A41D 1/04* | (2006.01) | |
| *A61F 7/10* | (2006.01) | |
| *A61F 7/00* | (2006.01) | |

(52) U.S. Cl.
CPC .......... *A41D 13/0058* (2013.01); *A41D 1/04* (2013.01); *A61F 7/103* (2013.01); *A41D 2400/46* (2013.01); *A61F 2007/0056* (2013.01); *A61F 2007/108* (2013.01)

(58) Field of Classification Search
CPC .. A41D 13/0058; A41D 1/04; A41D 2400/46; A61F 7/103; A61F 2007/0056; A61F 2007/108; F25D 2400/26
See application file for complete search history.

(56) References Cited

U.S. PATENT DOCUMENTS

| | | | | |
|---|---|---|---|---|
| 2002/0016984 A1* | 2/2002 | Poholski | ............ | A41D 13/0058 607/108 |
| 2009/0062892 A1* | 3/2009 | Ilcheva | .............. | A41D 13/0518 607/108 |
| 2010/0032458 A1* | 2/2010 | Shitaye | .................... | A45F 5/00 224/148.2 |

FOREIGN PATENT DOCUMENTS

WO  WO-2018165696 A1 * 9/2018

* cited by examiner

*Primary Examiner* — Cassey D Bauer
(74) *Attorney, Agent, or Firm* — Barry Choobin; Patent 360

(57) ABSTRACT

A dual-function vest for keeping the body cool and providing cool drinking water. The vest has multiple ice pockets dispersed throughout an area of the vest. The ice pockets are fluidly interconnected to each through fluid channels, wherein water can flow between the multiple ice pockets. A port can be provided in the vest to provide access to an inner volume of the vest. Water can be filled into the multiple ice pockets through the port and also water can be drawn through the port. A long tube can be connected to the port while the free end of the long tube can act as a drinking spout.

12 Claims, 5 Drawing Sheets

COOLING AND DRINKING VEST

CROSS-REFERENCE TO RELATED APPLICATIONS

This application claims priority from a U.S. Provisional Patent Appl. No. 63/322,373 filed on 22 Mar. 2022, which is incorporated herein by reference in its entirety.

FIELD OF INVENTION

The present invention generally relates to a cooling and drinking vest, and more particularly, the present invention relates to a dual-function vest with ice pockets for keeping the body cool and providing cool drinking water.

BACKGROUND

Exposure to hot weather conditions for a long time can lead to heatstroke which is a life-threatening condition. It is essential to keep the body temperature controlled in hot weather conditions. Moreover, proper hydration is essential to replenish fluid loss and prevent dehydration. Keeping the body cool and drinking a lot of water in hot weather is essential to prevent heatstroke and dehydration. For example, in outdoor activities, such as hiking in hot climates, people prefer to drink a lot of cool water to keep their bodies cool and hydrated. Moreover, any act which cools the body or having cold drinks also feels pleasant and desirable in hot weather. People often pour water on their bodies while being under the hot sun to keep the body temperature normal. Also, the use of cool air from portable fans is another way to keep the body temperature normal in climates.

However, when outdoors, the availability of various means to keep the body cool and hydrated are limited or may not be readily available. For example, during hiking, a person must carry a water bottle or a portable ice cooler, or a fan which is not desirable being tedious and occupying the free hand of a person.

Thus, a need is appreciated for a device that can keep the body cool when outdoors and also provide readily accessible cool drinking water.

SUMMARY OF THE INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a vest that can store ice.

It is another object of the present invention that the vest can provide uniform cooling of the human body.

It is another object of the present invention that the melted ice or water in the vest could be drunk directly.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting to embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

Figure 1:
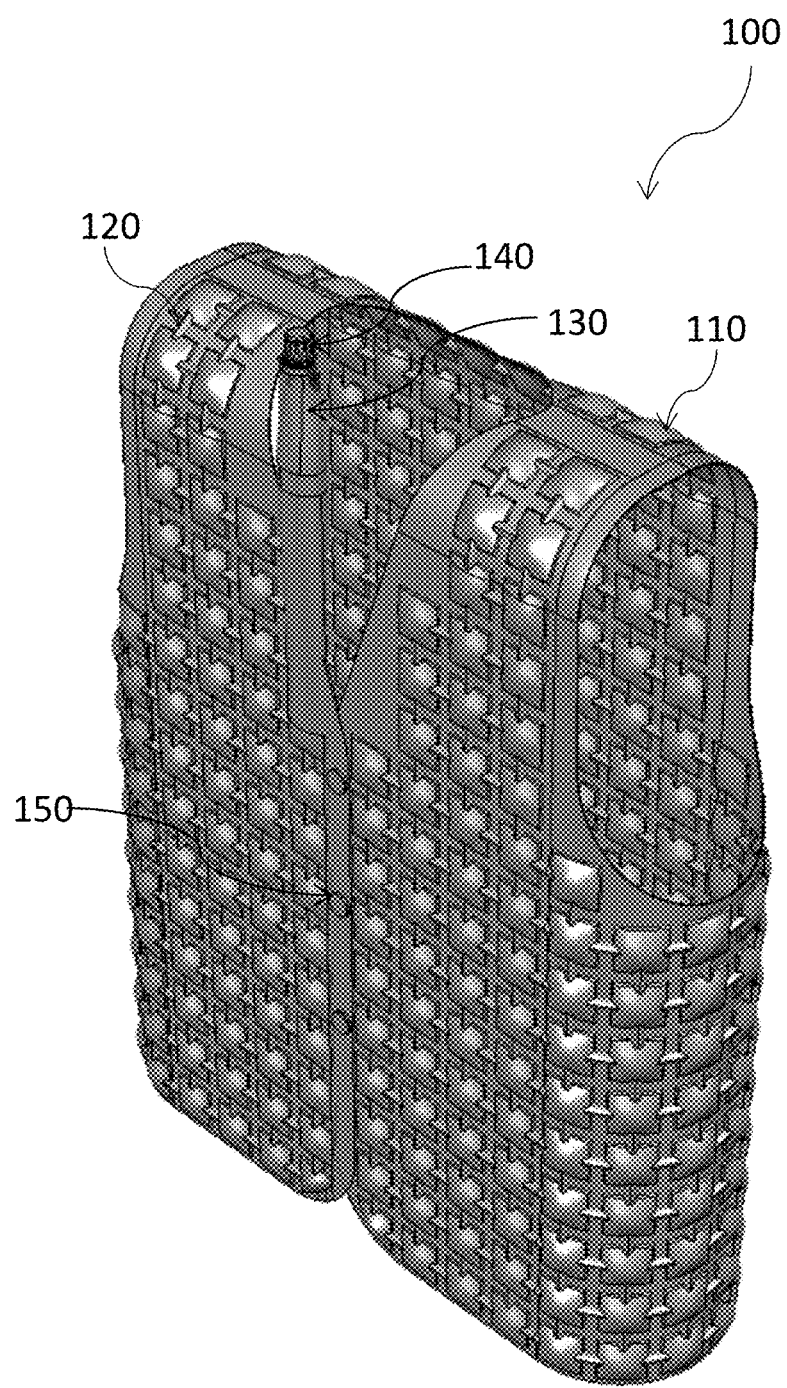
FIG. 1 is a perspective view of a vest, according to an exemplary embodiment of the present invention.
Figure 2:
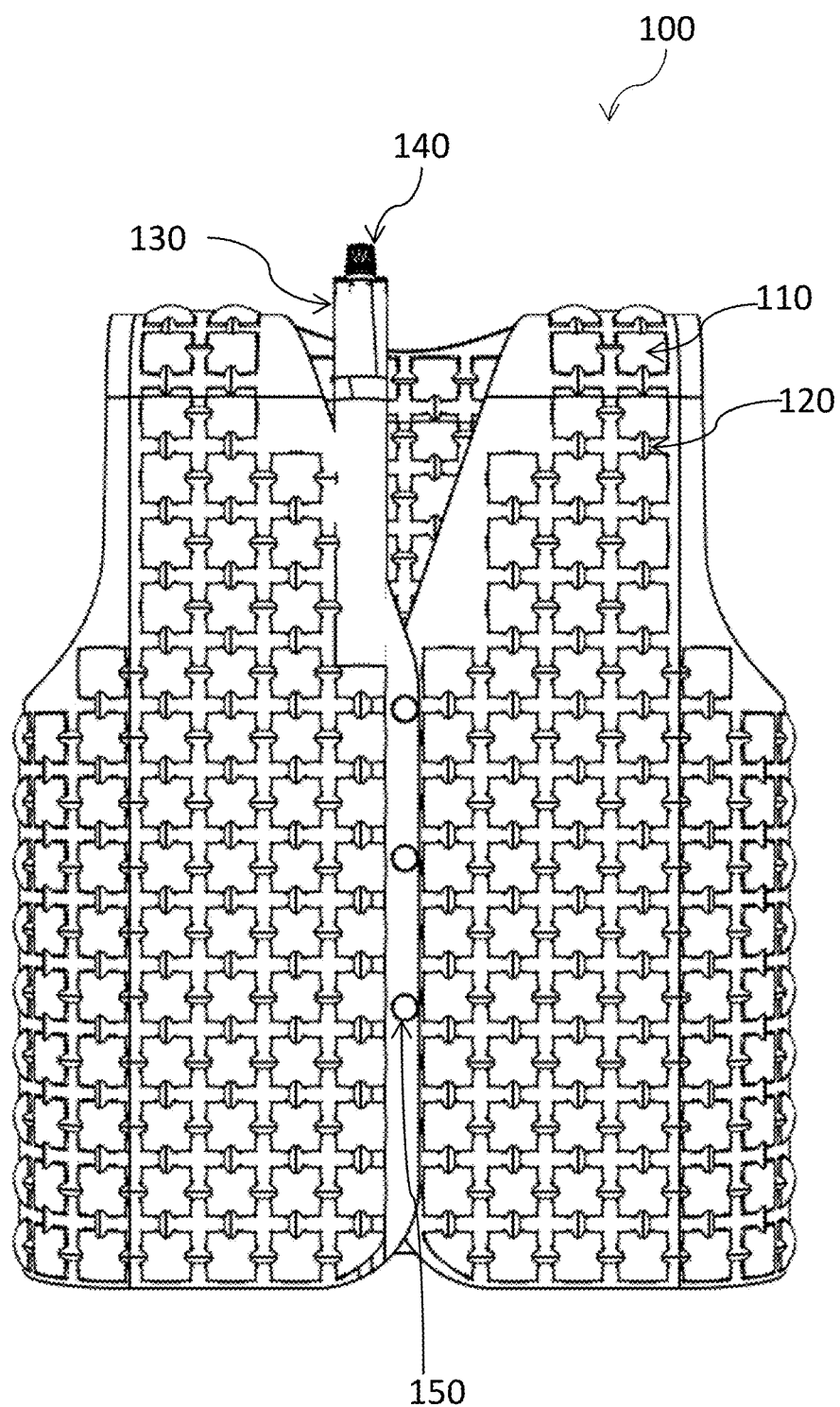
FIG. 2 is a front view of the vest, according to an exemplary embodiment of the present invention.
Figure 3:
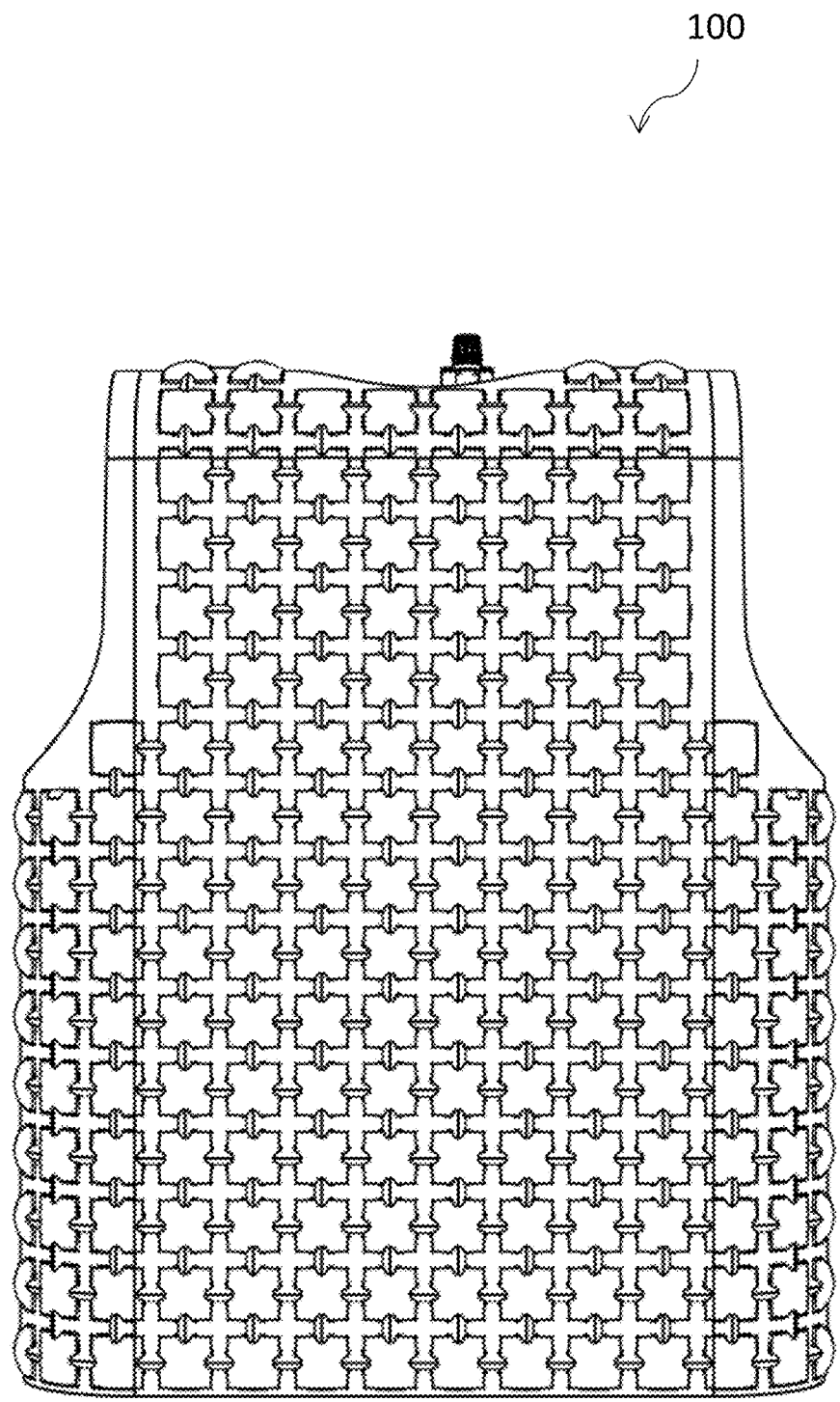
FIG. 3 is a rear view of the vest, according to an exemplary embodiment of the present invention.

Disclosed is a vest that can be worn over a torso of a human body for keeping the body cool and also providing a readily available source of cool drinking water. Referring to FIGS. 1-3 which shows a vest 100 as a wearable device that can be worn over a torso of the human body and includes at least a neck opening and two openings for the two hands. The vest has no sleeves and can cover at least the front and back of the torso. FIG. 1 shows a vest as an embodiment of the present invention is for illustration only, however, any type of garment is within the scope of the present invention. For example, trousers, neck wraps, hats, and the like are within the scope of the present invention.

The vest 100 can include several ice pockets 110 or ice pockets are dispersed throughout the area of the vest. The ice pockets 110 can be interlinked through fluid channels 120 that allow the fluid flow between the adjacent ice pockets. The ice pockets in the vest can be connected to each other through fluid channels, such as the fluid can enter from one ice pocket into other ice pockets. FIG. 1 shows an ice pocket connected through four fluid channels to four adjacent ice pockets.

The vest 100 can further include a drinking spout 140 connected to an inner volume of the vest through a tube 130. The tube 130 can extend from the bottom area of the vest, such as melted ice can be drawn as cool water through tube 130. The drinking spout 140 and the tube 130 can act as an input port and an output port for the vest to fill in water and draw water from the inner volume of the vest. From the input port, the water can flow directly and indirectly to the ice pockets. Alternatively, a separate input port and an output port can be provided, wherein the input port, the output port, and the several pockets are in fluid communication with each other.

In one implementation, water can be filled through a single input port, wherein the water flows into the ice pockets. The ice pockets can be interconnected through fluid channels, so that water can flow from one ice pocket to adjacent ice pockets and from the adjacent ice pockets to further ice pockets. Water from the melted ice can collect in the bottom of the vest and can be drawn from the output port. In another implementation, the ice pockets can be divided into several sections and the several sections can be fluidly connected to the input port and the output port.

Figure 4:
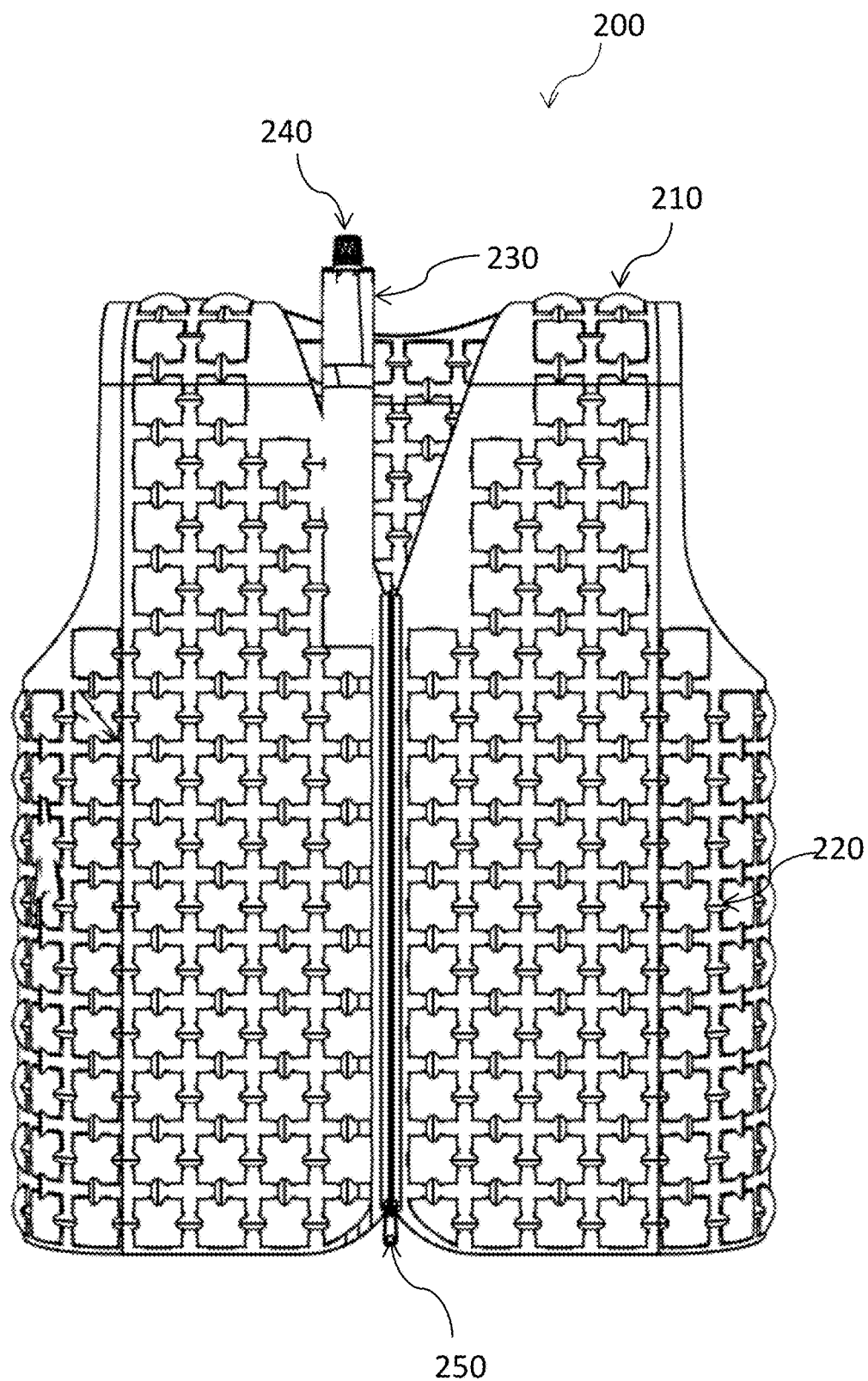
FIG. 4 is a front view of another embodiment of the vest, according to an exemplary embodiment of the present invention.

Fasteners can be used to close the vest on the front side. FIG. 2 shows buttons 150 as the fasteners on the front side of the vest that can be used to secure two sections of the vest. To wear the vest, the fasteners can be unbuttoned, and then the vest can be worn. Thereafter, the fasteners can be buttoned to secure the vest. Instead of buttons, any other type of fastener can also be used without departing from the scope of the present invention. FIG. 4 shows a vest 200 that has ice pockets 210, fluid channels 220, tube 230, drinking spout 240, and a zipper 250 as a fastener.

Figure 5:
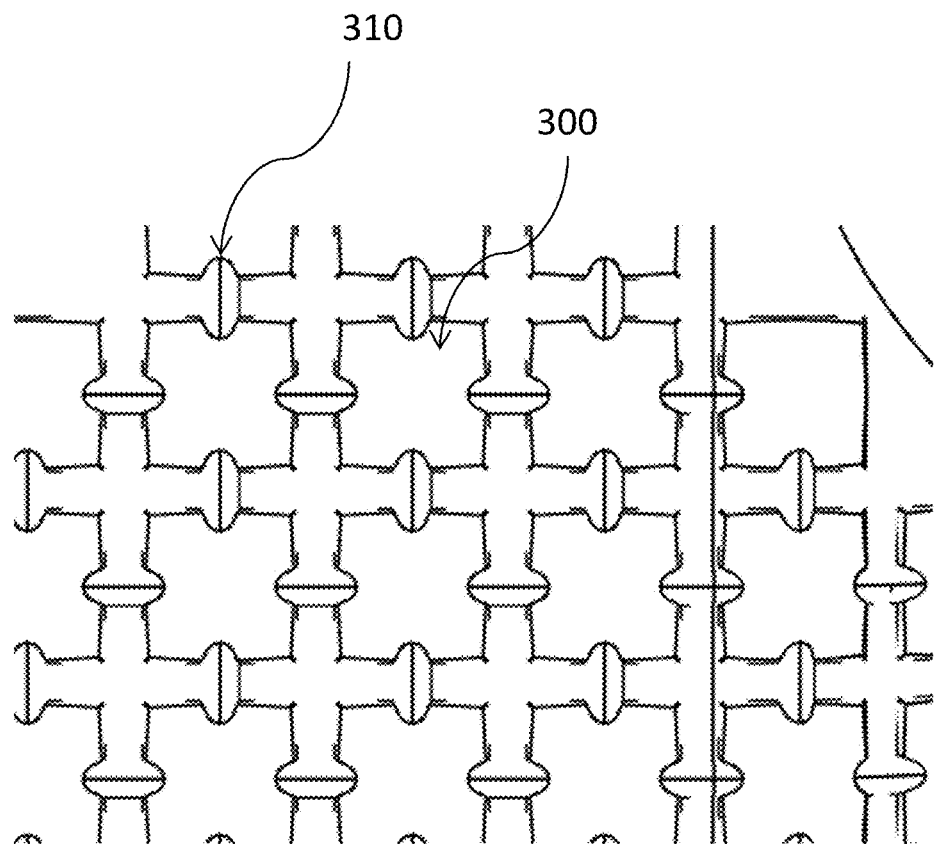
FIG. 5 is an enlarged view of a section of the vest showing ice pockets and fluid channels, according to an exemplary embodiment of the present invention.

In one implementation, the vest can be made from two plies that can be bonded to each other to form ice pockets like bubble wraps and fluid channels between the ice pockets. More clearly shown in FIG. 5, which is an enlarged view of a section of the disclosed vest. Ice pockets 300 can be similar to air pockets in bubble wrap. Each ice pocket is fluidly connected to at least one ice pocket through a fluid channel 310.

Also shown in FIGS. 1, the ice pockets are formed in continuous rows and columns, and the ice pockets are fluidly connected to four adjacent ice pockets. It is understood, however, that not all ice pockets have four fluid channels, for example, the ice pockets formed at the edges can have one or two fluid channels. Moreover, the shape of ice pockets and the number of fluid channels can be varied without departing from the scope of the present invention. In certain implementations, a bottom row of ice pockets in the vest can be a single continuous pocket in which water from melted ice can get collected, and the single continuous bottom pocket can connect to multiple ice pockets in the upper adjacent row through multiple fluid channels.

In certain implementations, a long tube at one end can be connected to a port in the vest, and another end of the long tube can be configured as a drinking spout. The drinking spout can be configured to be pressed between the lips and a suction force can be applied to draw the water collected in the vest from the melting of the ice.

In use, the user can fill an empty vest with water through the port, wherein the water fills into one or more ice pockets directly connected to the port. From these ice pockets, the water further flows into connected ice pockets through the fluid channels. Once, the liquid can be filled in all of the ice pockets, the port can be closed and the vest with water-filled can be frozen. The adjacent pockets can be separated by some bonded space in between that provides suitable flexibility to the frozen vest. Besides the water being frozen, an individual could easily wear the vest. The vest with the ice can keep the human body cool, wherein the ice can draw heat from the body and melt. The water from the melted ice can collect in the bottom pockets, and the user can drink the cool water from the vest using the spout. For example, during hiking, a person can wear the disclosed vest to keep the body cool and can also drink cool water from the vest avoiding the need to carry water bottles.

In certain implementations, the disclosed vest can be used in cold weather to keep the body warm. The inner volume of the vest, including the ice pockets, can be filled with hot water or warm water. The inner layer of the vest that comes in contact with the body of a wearer can be made from heat-resistant material that can distribute heat uniformly to the body and preferably prevent hot spots and flashes. Besides filling with hot water, the vest can provide warmth rather than hot flashes. The outer layer of the vest can be made from insulative material that prevents the loss of heat to the environment. In certain implementations, the same vest can be used for both hot and cold applications. The outer layer can be insulative to prevent heat exchange with the environment, thus keeping hot water hot for a longer duration and keeping the ice or cool water cooler for a longer duration. The inner layer can provide for heat distribution so that both heat application and cold application are soft to the person without acute hot flashes or acute cold flashes.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A wearable device comprising:
   a garment;
   a plurality of ice pockets dispersed throughout the garment, the plurality of ice pockets are fluidly interconnected to each other through fluid channels, wherein fluid can flow between adjacent ice pockets, wherein each ice pocket of one or more ice pockets of the plurality of ice pockets is fluidly connected to four adjacent ice pockets of the plurality of ice pockets through four fluid channels;
   at least one port connected to one or more ice pockets of the plurality of ice pockets, wherein the at least one port is positioned at a bottom of the garment; and a tube that has a proximal end and a distal end, the proximal end is coupled to the at least one port and the distal end is configured as a drinking spout.

2. The wearable device according to claim 1, wherein water can be filled into an inner volume of the garment through the port, and water can be drawn from the inner volume of the garment through the port.

3. The wearable device according to claim 1, wherein the garment is a vest, the vest has a neck opening and two arms openings.

4. The wearable device according to claim 3, wherein the vest is made from two plies bonded together forming the plurality of ice pockets and fluid channels, wherein an inner plie of the two plies is made of heat-resistant material and an outer plie of the two plies is made of an insulative material.

5. The wearable device according to claim 4, wherein the vest further comprises a plurality of buttons for securing the vest over a torso of a wearer.

6. The wearable device according to claim 4, wherein the vest further comprises a zipper for securing the vest over a torso of a wearer.

7. A method for maintaining body temperature, the method comprises:
providing a vest, the vest has at least a neck opening and two arms openings, the vest further comprises:
a plurality of ice pockets dispersed throughout an area of the vest, the plurality of ice pockets are fluidly interconnected through fluid channels, wherein fluid can flow between adjacent ice pockets of the plurality of ice pockets through the fluid channels, wherein each ice pocket of one or more ice pockets of the plurality of ice pockets is fluidly connected to four adjacent ice pockets of the plurality of ice pockets through four fluid channels,
at least one port connected to one or more ice pockets of the plurality of ice pockets, wherein the at least one port is positioned at a bottom of the garment, and
a tube that has a proximal end and a distal end, the proximal end is coupled to the at least one port and the distal end is configured as a drinking spout.

8. The method according to claim 7, wherein the method further comprises:
filling water into the vest, wherein the plurality of ice pockets are filled with water;
freezing the water filled vest;
wearing the frozen vest over a torso of a wearer; and
drinking water melted in the frozen vest through the drinking spout.

9. The method according to claim 8, wherein the water is filled into an inner volume of the vest through the port, and the water for drinking is drawn from the inner volume of the vest through the port.

10. The method according to claim 7, wherein the vest is made from two plies bonded together forming the plurality of ice pockets and fluid channels, wherein an inner plie of the two plies is made of heat-resistant material and an outer plie of the two plies is made of an insulative material.

11. The method according to claim 10, wherein the vest further comprises a plurality of buttons for securing the vest over a torso of a wearer.

12. The method according to claim 10, wherein the vest further comprises a zipper for securing the vest over a torso of a wearer.

* * * * *